(12) United States Patent
Van Willigenburg

(10) Patent No.: US 10,190,060 B2
(45) Date of Patent: Jan. 29, 2019

(54) PROCESS FOR INCREASING PROCESS FURNACES ENERGY EFFICIENCY

(71) Applicants: Saudi Basic Industries Corporation, Riyadh (SA); SABIC Global Technologies B.V., PX Bergen Op Zoom (NL)

(72) Inventor: Joris Van Willigenburg, Geleen (NL)

(73) Assignees: SAUDI BASIC INDUSTRIES CORPORATION, Riyadh (SA); SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 15/120,701

(22) PCT Filed: Dec. 23, 2014

(86) PCT No.: PCT/EP2014/079172
§ 371 (c)(1),
(2) Date: Aug. 22, 2016

(87) PCT Pub. No.: WO2015/128035
PCT Pub. Date: Sep. 3, 2015

(65) Prior Publication Data
US 2017/0022429 A1    Jan. 26, 2017

(30) Foreign Application Priority Data

Feb. 25, 2014    (EP) .................................... 14156624

(51) Int. Cl.
*C10G 9/36* (2006.01)
*C10G 9/14* (2006.01)
(Continued)

(52) U.S. Cl.
CPC ................ *C10G 9/36* (2013.01); *C07C 5/327* (2013.01); *C10G 9/002* (2013.01); *C10G 9/14* (2013.01); *F02C 6/18* (2013.01); *Y02E 20/14* (2013.01)

(58) Field of Classification Search
None
See application file for complete search history.

(56) References Cited

U.S. PATENT DOCUMENTS 1,912,938 A * 6/1933 Grebe ....................... F22B 3/02
122/1 R
4,172,857 A    10/1979 Pavilon
(Continued)

FOREIGN PATENT DOCUMENTS

JP    H06-272515        9/1994
JP    H0979506 A        3/1997
(Continued)

OTHER PUBLICATIONS

International Search Report and Written Opinion of corresponding International Application No. PCT/EP2014/079172, dated Mar. 23, 2015; 9 pages.
(Continued)

*Primary Examiner* — Tam M Nguyen
(74) *Attorney, Agent, or Firm* — Norton Rose Fulbright US LLP

(57) ABSTRACT

A process for increasing furnace energy efficiency through gas turbine integration by using turbine exhaust gas, wherein a hydrocarbon feed is heated in a furnace.

12 Claims, 1 Drawing Sheet

(51) Int. Cl.
*C10G 9/00* (2006.01)
*F02C 6/18* (2006.01)
*C07C 5/327* (2006.01)

(56) References Cited

U.S. PATENT DOCUMENTS

| | | |
|---|---|---|
| 6,153,087 A | 11/2000 | Bigeard et al. |
| 6,237,337 B1 | 5/2001 | Bronicki et al. |
| 6,270,654 B1 | 8/2001 | Colyar et al. |
| 7,214,308 B2 | 5/2007 | Colyar |
| 7,704,377 B2 | 4/2010 | Duddy et al. |
| 7,938,952 B2 | 5/2011 | Colyar et al. |
| 8,926,824 B2 | 1/2015 | Morel |
| 9,005,430 B2 | 4/2015 | Fournier et al. |
| 9,840,674 B2 | 12/2017 | Weiss et al. |
| 2007/0234702 A1* | 10/2007 | Hagen .................... B60H 1/032 60/39.01 |
| 2008/0093262 A1 | 4/2008 | Gragnani et al. |
| 2013/0001132 A1 | 1/2013 | Baumgartner et al. |
| 2014/0299515 A1 | 10/2014 | Weiss et al. |
| 2016/0122666 A1 | 5/2016 | Weiss et al. |

FOREIGN PATENT DOCUMENTS

| | | |
|---|---|---|
| WO | 90/06351 A1 | 8/1990 |
| WO | 91/15665 A1 | 10/1991 |
| WO | 2010/077461 A1 | 7/2010 |
| WO | WO 2016/146326 | 9/2016 |

OTHER PUBLICATIONS

Office Action issued in Japanese Patent Application No. 2016-554181, dated Jun. 5, 2018.

\* cited by examiner

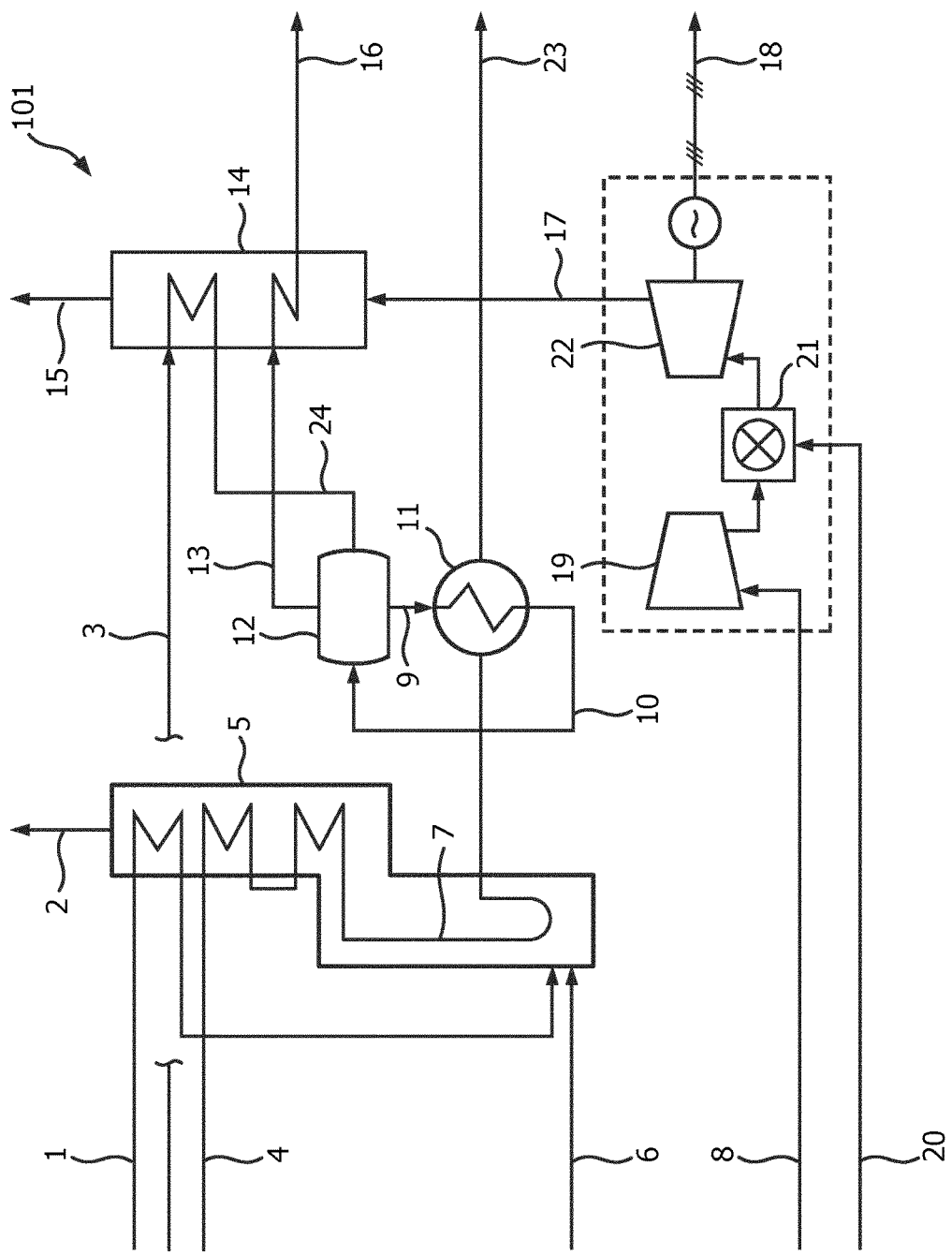

PROCESS FOR INCREASING PROCESS FURNACES ENERGY EFFICIENCY

CROSS-REFERENCE TO RELATED APPLICATIONS

This application is a national phase under 35 U.S.C. § 371 of International Application No. PCT/EP2014/079172, filed Dec. 23, 2014, which claims the benefit of priority to European Patent Application No. 14156624.0, filed Feb. 25, 2014, the entire contents of each of which are hereby incorporated by reference in their entirety.

TECHNICAL FIELD AND BACKGROUND OF THE INVENTION

The present invention relates to a process for increasing process furnaces energy efficiency through gas turbine integration by using turbine exhaust gas, wherein a hydrocarbon feed is heated in a furnace. More in detail, the present invention relates to the increased energy efficiency of steam cracking by gas turbine integration.

U.S. Pat. No. 4,172,857 relates to a non-catalytic cracking process employing a pressurized riser-type thermal cracker heated by hot agglomerated ash particles circulated from a separate coal burning power producing combustion unit. Compressed air from a compressor passes through a conduit to coils of a heat exchanger and then passes to the main air supply conduit and to the branch conduit which supplies high velocity air to the recycle conduit means. The flue gases or combustion gases from the combustion unit pass upwardly through the outlet to the duct. The gases leaving the cyclone pass to the flue gas duct which carries the ash-free flue gases to the steam generator and a superheater. The gases then pass to the inlet of the gas turbine and to the heat exchanger. A steam turbine and an electric motor-generator are connected to the turbine and the compressor to assist in starting and the latter for generating electricity from excess power available after starting. The superheater and heat exchanger recover heat energy from the flue gases to provide steam and to preheat the liquid hydrocarbon feedstock and the air so that the flue gases are cooled. Boiler feed water introduced to the coils of the heat exchanger are preheated, and returned to a steam drum. Water from the steam drum is fed to a conventional heat exchanger heated by the cracked gases to form steam which is returned to the steam drum. Steam from the drum passes to the superheater coil, and superheated steam is discharged. The technology described here has a compressor compressing ambient air to a combined (catalyst) regeneration process/process heat supply. This compressor is driven by a turbine expanding a hydrocarbon gas from the process. The work produced/required by turbine and compressor are directly related to the process.

WO90/06351 relates to a process for inhibiting coke formation during the vaporization of heavy hydrocarbons by preheating such hydrocarbons in the presence of a small, critical amount of hydrogen in the convection section of a conventional tubular furnace. The technology described here is a technology to prevent coke formation in (steam) cracking furnaces and does not relate to a technology that is more energy efficient by the combining electricity production with steam cracking.

WO2010/077461 relates to a process to prevent coke formation and allows for processing of heavier hydrocarbon feed in cracking furnaces, comprising a process for cracking a hydrocarbon feedstream containing non-volatile components in a hydrocarbon cracking furnace having upper and lower convection heating sections within a flue of the furnace, a radiant heating section downstream of and connected to said lower convection heating section, a transfer line exchanger downstream of and connected to said radiant heating section, a furnace box containing furnace burners and said radiant heating section, and a vapor/liquid separator vessel connected between the upper and lower convection heating sections. The technology described here is a technology to prevent coke formation and allows for processing of heavier hydrocarbon feed in cracking furnaces and this reference does not describe a technology that is more energy efficient by the combining electricity production with steam cracking.

US patent application No 2013/001132 relates to a process and apparatus for producing olefins in a pyrolysis furnace employing TLEs to cool the pyrolysis gases, comprising injecting an amount of wetting fluid into the tubes of TLEs to keep the tube wall wetted thus to prevent coking, wherein the wetted-wall TLE can generate high pressure steam.

JPH0979506 relates to a method for injecting hydrazine in an exhaust heat recovery boiler for preventing the occurrence of pitting in the heat transfer tube of such an exhaust heat recovery boiler.

WO91/15665 relates to a method of adjusting the heat generation in a sulphate pulp process to correspond to the heat consumption by injecting excess steam into a gas turbine combustor or into the exhaust gas thereof.

U.S. Pat. No. 6,237,337 relates to retrofit equipment for reducing the consumption of fossil fuel by a power plant using solar insolation, wherein the power plant includes a waste heat boiler in the form of a series of heat exchanger coils and receiving hot exhaust gases. After exiting the boiler, the then heat-depleted exhaust gases are vented to the atmosphere. Vaporization of water in the heat exchange coils takes place in multiple stages, producing steam which is applied to a steam turbine coupled to a generator. The turbine expands the steam and drives a generator producing power from the generator and expanded steam from the turbine exhaust. A condenser condenses the expanded steam to condensate and the condensate is returned to the boiler to complete the water loop. Steam is applied to superheater coils producing superheated steam that is applied to the turbine.

Steam cracking, also referred to as pyrolysis, has long been used to crack various hydrocarbon feedstocks into olefins, preferably light olefins such as ethylene, propylene, and butenes. Conventional steam cracking utilizes a pyrolysis furnace which has two main sections: a convection section and a radiant section. The hydrocarbon feedstock typically enters the convection section of the furnace as a liquid (except for light feedstocks which enter as a vapour) wherein it is typically heated and vaporized by indirect contact with hot flue gas from the radiant section and by direct contact with steam. The vaporized feedstock and steam mixture is then introduced into the radiant section where the cracking takes place. The resulting products, including olefins, leave the pyrolysis furnace for further downstream processing, including quenching.

In an energy conversion process, for example operated by Lummus Technology, the steam cracker energy efficiency is increased through gas turbine integration wherein gas turbine flue gas (approx. 400-650° C., depending on gas turbine type, containing approximately 13-15% vol oxygen) is used as combustion air for the cracking furnaces. The gas turbine integration with ethylene plant comprises, inter alia, the use of turbine exhaust gas as a feed for combustion air distribution header.

Some aspects relating to this technology are: energy savings from combined heat and power (CHP) increase when more heat can be supplied to the process. The heat supply to the process (and thus energy savings potential) is limited by the combustion air requirements of the steam cracking furnaces, the size of the gas turbine is limited by the combustion air requirements in the furnaces, limiting possible scale advantages of larger gas turbines. This means that the operation scale of this technology is dictated by the intimate technical relationship between the steam cracking furnaces and the combined heat and power (CHP) resulting in some possible negative technical consequences.

This means that in such a construction a gas turbine trip has a significant disturbance on the cracking conditions resulting in consequences for the whole back end of the plant. This technology of integration results in additional steam production by the cracking furnaces. This limits the application potential of other energy savings options such as CHP plants or on sites with a balanced steam supply and consumption. Thus additional steam generated in the cracking furnaces will replace efficient steam generation from an on-site CHP plant resulting in less net savings.

An object of the present invention is to provide a method for increasing steam cracker energy efficiency through gas turbine integration in which method the furnace processes are run separately from the gas turbine processes.

BRIEF SUMMARY OF THE INVENTION

Another object of the present invention is to provide a process for increasing steam cracker energy efficiency through gas turbine integration in which process the negative effect of a gas turbine trip on the whole system of steam cracker and gas turbine is minimized.

Another object of the present invention is to provide a process for increasing steam cracker energy efficiency through gas turbine integration by using turbine exhaust gas, in which process super heated steam is produced in an energy efficient way.

Another object of the present invention is to provide a process for increasing steam cracker energy efficiency through gas turbine integration by using turbine exhaust gas, in which the heat from turbine exhaust gas is used for heating boiler feed water.

The present invention relates thus to a process for increasing steam cracker energy efficiency through gas turbine integration by using turbine exhaust gas, wherein a hydrocarbon feed is heated in a furnace, said process comprising the following steps:

i) feeding furnace combustion air to the burners of said furnace together with furnace fuel to provide high temperature heat to said furnace;

ii) cooling the hydrocarbon feed thus processed by using water from a steam drum under the formation of water vapour;

iii) returning the mixture of water and water vapour thus formed to said steam drum;

iv) withdrawing of saturated high-pressure steam from said steam drum and feeding said saturated high-pressure steam to a heat recovery unit;

v) feeding said turbine exhaust gas to said heat recovery unit for converting said high-pressure steam into super heated high pressure steam.

The present process thus provides a physical separation of the air systems of CHP unit and process furnaces. By feeding said turbine exhaust gas to said heat recovery unit in stead of directing said turbine exhaust gas to the radiant section of the furnaces a situation of decoupling CHP unit and process furnaces is realized according to the present method.

The present invention is thus related to a method for decoupling the gas turbine from the process furnace. This decoupling has the following advantages:

i) it reduces the duty in the convection section of the process furnace, resulting is excess heat available in the convection section, that is now used to preheat combustion air resulting in (1) less fuel gas consumption and (2) higher combustion temperatures in the process furnace making more high quality heat available and less low quality "waste" heat to be recovered in the convection section of the process furnace. This is an energy efficiency benefit.

ii) the utility (turbine/compressor) system is not interfering with the process. Especially in the discussed U.S. Pat. No. 4,172,857 a trip of either compressor (4), gas turbine (5), motor/generator (81) and/or steam turbine (80) (these reference numbers are retrieved from FIG. 1 in U.S. Pat. No. 4,172,857) will result in a stop of the entire process, since their operation is vital to the process (supply of compressed air to the regeneration unit will stop, stopping the process). While the process according to the present invention can continue (although at lower energy efficiency and possibly lower capacity).

The indirect integration as disclosed in the present invention does not affect the cracking conditions in the case of a trip on the gas turbine.

In fact, the present heat recovery unit is decoupled from the furnaces and such a (disconnected) position of the heat recovery unit consequently results in an independent control thereof. Such a separation of the heat recovery unit has the advantageous effect of decoupling of the scale of both units and enables a more advantageous CHP. Moreover, the energy efficiency of the preparation of boiler feed water, and thus the preparation of super heated high pressure steam, can be highly increased by using the heat capacity of not only the hot flue gasses from the furnace but from the heat recovery unit itself as well. From an operational point of view one can see a big advantage when using the present invention since an operational upset or trip of one of the units, for example the gas turbine section, does not mean shut-down of the other unit, for example the furnace system, and vice versa.

According to the present method a gas turbine generator (GTG) produces electricity and hot flue gasses. The hot flue gasses are used by the heat recovery unit (HRU) to superheat the saturated steam from the steam drum in the super heater (SH) section of the HRU.

According to the present process the furnace is preferably chosen from the group of steam cracker furnace, propane dehydrogenation furnace and butane dehydrogenation furnace.

According to a preferred embodiment of the present invention the furnace is a steam cracker furnace. In such a steam cracker furnace high temperature heat according to step i) is provided to the radiant section of said cracking furnace for pyrolysis of the hydrocarbon feed present in said radiant section under cracking conditions.

A steam cracker furnace consists out of a radiant section and a convection section. In the convection section the hydrocarbon feed is preheated (FPH), in the case of liquid hydrocarbon feed evaporated (FPH) and further heated (FH) and cracked in the radiant coils of the radiant section. In the present invention heat recovery takes place by preheating the combustion air (APH). After leaving the radiant section the gas is rapidly cooled by a transfer line exchanger (TLE) and cooling is provided by water from the steam drum. In the steam drum water and steam are separated. The steam is superheated in the Super Heater (SH).

The present process preferably comprises feeding boiler feed water to said heat recovery unit and feeding the boiler feed water thus preheated to said steam drum. According to another embodiment the present process further comprises preheating boiler feed water through hot flue gasses from a furnace and feeding the boiler feed water thus preheated to said steam drum.

In addition, it is preferred to carry out step ii) by using a transfer line exchanger (TLE).

According to a preferred embodiment of the present process the heat recovery unit further comprises an evaporator and/or a steam generator.

It is additionally preferred that the heat recovery unit comprises one or more duct burners for providing additionally heating capacity for additional steam generating capacity.

Furthermore the present process further comprises one or more fresh air suppliers for providing air to said one or more burners.

The process according to the invention additionally comprises one or more economizers, steam generators, steam drums and super heaters, operated at lower pressures to produce heat medium and/or low pressure steam.

In the present process it is also possible to heat process liquids or gasses by feeding said process liquids or gasses to said heat recovery unit.

The heat recovery unit can be equipped with an evaporator. In the case of a trip of some or all of the cracking furnaces some steam production will continue. In addition, the heat recovery unit can be equipped with an evaporator and supplementary firing to allow for additional steam production and backup capacity in the case of the trip of one or more cracking furnaces. It is also possible to provide the heat recovery unit with a steam generator, an evaporator and fresh air firing to allow for continued operation in the case of a trip of the gas turbine. Moreover, instead of the heating of boiler feed water, other process liquids or gasses could also be heated in this section of the heat recovery unit. The steam cracking furnaces can be equipped with flue gas recirculation to decrease the combustion temperature resulting in lower NOX emissions. Steam cracking furnaces can be equipped with SCR NOX reduction.

The invention will be described in further detail below and in conjunction with the attached drawing.

BRIEF DESCRIPTION OF THE DRAWINGS

FIG. 1 is a schematic illustration of an embodiment of the process of the invention.

Referring now to the process and apparatus 101 schematically depicted in FIG. 1, there is shown a process for increased energy efficiency of steam cracking by gas turbine integration.

DETAILED DESCRIPTION OF THE INVENTION

Combustion air 1 is sent to a section of furnace 5. In furnace 5 stream 4, comprising process feed, is heated in a first preheating section and further heated and cracked in the radiant coils 7 of the radiant section of furnace 5. Furnace 5 is heated through stream 6, comprising fuel. Combustion air 1 is preheated through hot flue gasses 2 from cracking furnace 5. It is also possible (not shown) to preheat combustion air 1 in a section of heat recovery unit 14. The cracked hydrocarbon feed coming from cracking furnace 5 is rapidly cooled by a transfer line exchanger (TLE) 11. Cooling is provided by water 9 from steam drum 12. In steam drum 12 water and steam are separated and the steam 13 produced in steam drum 12 is sent to a heat recovery unit 14. Saturated high pressure steam 13 is converted in super heated high pressure steam 16 after leaving heat recovery unit 14. In transfer line exchanger 11 water 9 coming from steam drum 12 is converted into a mixture 10 of water and steam and returned to steam drum 12. Boiler feed water 3 is heated in a section of heat recovering unit 14, which section is also called economizer. It is also possible (not shown) to preheat boiler feed water 3 through hot flue gasses 2 from cracking furnace 5. After heating boiler feed water 3 in heat recovering unit 14, the heated water 24 is sent to steam drum 12.

Electricity 18 is generated in a generator connected to turbine 22, which turbine 22 is connected to compressor 19. Ambient air 8 is sent to compressor 19. In combustion chamber 21 fuel 20 is mixed with high pressure air coming from compressor 19 and combusted. The high pressure combustion products are expanded in turbine 22. The exhaust gas from turbine 22 is sent to heat recovery unit 14. It is also possible to provide the heat recovery unit 14 with one or more economizers, steam generators, steam drums and super heaters (not shown), operated at lower pressures to produce heat medium and/or low pressure steam.

FIG. 1 shows an embodiment of a steam cracker furnace 5 but the present method can also be carried out for other furnaces, such as propane dehydrogenation furnaces and butane dehydrogenation furnaces.

The invention claimed is:

1. A process for increasing process furnaces energy efficiency through gas turbine integration by using turbine exhaust gas, wherein a hydrocarbon feed is heated in a furnace, said process comprising the following steps:
   i) feeding furnace combustion air to burners of said furnace together with furnace fuel to provide high temperature heat to said furnace;
   ii) cooling the hydrocarbon feed thus processed by using water from a steam drum under the formation of water vapour from some of the water;
   iii) returning the mixture of water and water vapour thus formed to said steam drum;
   iv) withdrawing saturated high-pressure steam from said steam drum and feeding said saturated high-pressure steam to a heat recovery unit; and
   v) feeding said turbine exhaust gas to said heat recovery unit for converting said high-pressure steam into super heated high pressure steam, thereby decoupling the gas turbine from the process furnace.

2. The process according to claim 1, wherein said furnace is from the group including a steam cracker furnace, a propane dehydrogenation furnace, and a butane dehydrogenation furnace.

3. The process according to claim 1, wherein said furnace is a steam cracker furnace and wherein in step i) high temperature heat is provided to a radiant section of said cracking furnace for pyrolysis of the hydrocarbon feed present in said radiant section under cracking conditions.

4. The process according to claim 1, further comprising preheating furnace combustion air through hot flue gasses from said furnace and/or hot flue gasses from said heat recovery unit.

5. The process according to claim 1 further comprising preheating boiler water through hot flue gasses from said heat recovery unit and feeding the boiler feed water thus preheated to said steam drum.

6. The process according to claim 1, further comprising preheating boiler water through hot flue gasses from a furnace and feeding the boiler feed water thus preheated to said steam drum.

7. The process according to claim 1, wherein step ii) is carried out using a transfer line exchanger (TLE).

8. The process according to claim 1, wherein said heat recovery unit further comprises an evaporator and/or a steam generator.

9. The process according to claim 1, wherein said heat recovery unit comprises one or more duct burners for providing additional heating capacity for providing super heated high pressure steam.

10. The process according to claim 9, further comprising one or more fresh air suppliers for providing air to said one or more burners.

11. The process according to claim 1, further comprising one or more economizers, steam generators, steam drums and super heaters, operated at lower pressures to produce heat medium and/or low pressure steam.

12. The process according to claim 1, further comprising heating process liquids or gasses by feeding said process liquids or gasses to said heat recovery unit.

* * * * *